United States Patent [19]

Bruins et al.

[11] 4,173,652
[45] Nov. 6, 1979

[54] PHARMACEUTICAL HYDROXAMIC ACID COMPOSITIONS AND USES THEREOF

[75] Inventors: Antonius H. N. M. Bruins; Gerlof Vollema, both of Ossk, Netherlands

[73] Assignee: Akzona Incorporated, Asheville, N.C.

[21] Appl. No.: 956,513

[22] Filed: Oct. 31, 1978

Related U.S. Application Data

[62] Division of Ser. No. 859,142, Dec. 9, 1977.

[30] Foreign Application Priority Data

Dec. 18, 1976 [NL] Netherlands ............... 7614113

[51] Int. Cl.² .......................................... A61K 31/165
[52] U.S. Cl. .................................................... 424/324
[58] Field of Search ....................... 424/320; 424/324

[56] References Cited

U.S. PATENT DOCUMENTS

| | | | |
|---|---|---|---|
| 3,479,396 | 11/1969 | Buu Hoi et al. ............... | 260/500.5 |
| 3,586,713 | 6/1971 | Buu Hoi et al. ............... | 260/500.5 |
| 3,600,437 | 8/1971 | Marshall ..................... | 260/500.5 H |
| 3,641,123 | 2/1972 | Hayman et al. ............... | 260/500.5 H |
| 3,890,377 | 6/1975 | Marshall ..................... | 424/315 |

FOREIGN PATENT DOCUMENTS

| | | | |
|---|---|---|---|
| 2347406 | 4/1974 | Fed. Rep. of Germany ... | 260/500.5 H |
| 1405767 | 9/1975 | United Kingdom ............ | 424/320 |

Primary Examiner—Douglas W. Robinson
Attorney, Agent, or Firm—Robert H. Falk; Charles A. Wendel; Francis W. Young

[57] ABSTRACT

New and useful phenylalkylcarbohydroxamic acids are disclosed of the formula

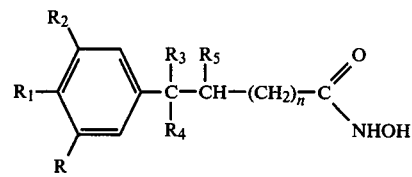

wherein:
(a) R is selected from the group consisting of alkoxy of one to six carbon atoms, alkenyloxy of two to six carbon atoms, alkyl of one to six carbon atoms, and benzyloxy;
(b) $R_1$ and $R_2$ are each selected from the group consisting of hydrogen, alkoxy of one to six carbon atoms, alkenyloxy of two to six carbon atoms, alkyl from one to six carbon atoms, and benzyloxy;
(c) $R_3$ and $R_4$ are selected from the group consisting of hydrogen or alkyl of one to six carbon atoms;
(d) $R_5$ is hydrogen or $R_5$ together with $R_3$ or $R_4$ represent methylene; and
(e) n signifies the number 0 to 1, and non-toxic salts thereof, which novel compounds exert a pronounced inhibition of blood platelet aggregation and accelerate the disaggregation of platelet aggregates already formed.

3 Claims, No Drawings

PHARMACEUTICAL HYDROXAMIC ACID COMPOSITIONS AND USES THEREOF

This is a division of application Ser. No. 859,142 filed Dec. 9, 1977.

BACKGROUND OF THE INVENTION

1. Field of the Invention

This invention disclosed is referring to the preparation of novel phenylalkylcarbohydroxamic acids substituted in the phenyl nucleus and to the use thereof in a pharmaceutical formulation; and relates to the field of hydroxamic acids employed for the inhibition of blood platelet aggregation.

2. Description of the Prior Art

Certain substituted phenylalkylcarbohydroxamic acids are known to those skilled in the art. Biologically active phenylmethylcarbohydroxamic acids possessing at least a substituent in the para-position ("p" position) are known from Belgian Pat. Nos. 648,892 and 661,226. Substituted phenylvinylcarbohydroxamic acids have furthermore been described in the Belgian Pat. No. 701,983. From the numerous publications with respect to these known hydroxamic acid derivatives which have appeared in the literature, such as 211 NATURE 752 (1966), 18 ARZNEIMITTELFORSCHUNG 1404 (1968), and J. MED. CHEM. 13, 211 (1970), it is obvious that a predominant characteristic of these compounds is a pronounced anti-inflammatory activity, with possible side-effects in the CNS field, such as a sedative action. Studies of the structure-activity relationships have inter alia shown that the anti-inflammatory activity is restricted to the hydroxamic acids derived from substituted phenylacetic acid derivatives and to a less extent from cinnamic acid derivatives. It is emphatically stated in 13 J. MED. CHEM. 211 (1970) that hydroxamic acids derived from substituted phenylpropionic acid derivatives no longer show any anti-inflammatory activity. Hence, a need arose in the art to (1) abolish the anti-inflammatory activity of such hydroxamic substituted acids; (2) not to retain sedative properties; (3) not to intensify CNS activity; while (4) trying to utilize any blood platelet aggregative inhibition properties.

Also it may be noted in 18 ARZNEIMITTELFORSCHUNG 1404 (1968) that removal or blockage of the hydroxylamine function (of the hydroxamic acid concerned) also causes to a great extent the anti-inflammatory activity to disappear. This statement is more or less confirmed by (1) the U.S. Pat. No. 3,190,800, which teaches that ethers of a large group of hydroxamic acids (including phenylalkylcarbohydroxamic acids) are depressives, and by (2) the French Pat. No. 1,332,352, which teaches that lower alkyl ethers of the hydroxamic acid derived from 3,4,5-tri-alkoxy-substituted cinnamic acid are sedatives.

On the basis of the above information, a conclusion that conversion to an ether group of the known hydroxamic acids (derived from substituted phenylacetic acid and substituted cinnamic acid) abolishes the anti-inflammatory activity, but considerably intensifies CNS activity, would be justified to one skilled in the art.

Additional patents of interest are U.S. Pat. Nos. 3,890,377 and 3,972,934 to Winston S. Marshall. Both U.S. Pat. Nos. 3,972,934 and 3,890,377 disclose selected 3-phenoxy-phenylalkyl amines (and the amides, alcohols, tetrazoles and carbamates related thereto) useful as anti-inflammatory agents with favourable analgesic and anti-pyretic side effects. Buu Hoi in U.S. Pat. No. 3,479,396 teaches the manufacture of a group of substituted arylaceto hydroxamic acids prepared by reacting hydroxylamine and alkyl acetate, in which the meta-position is optionally substituted. This U.S. patent corresponds to the two Belgium patents cited above. Finally, Nordman in U.S. Pat. No. 3,383,407 teaches the manufacture of 3,4,5-trimethoxybenzohydroxamic acids having sedative properties.

Surprisingly, it has now been found that hydroxamic acids derived from at least meta-substituted phenylpropionic acid and phenylbutyric acid derivatives exert a pronounced inhibition of blood platelet aggregation, while they also accelerate considerably the disaggregation of platelet aggregates already formed.

SUMMARY OF THE INVENTION

New and useful compounds represented by the general formula:

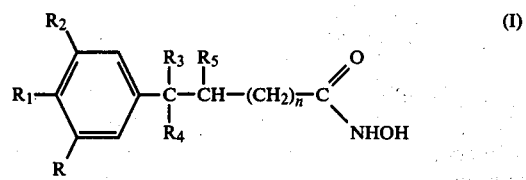

and non-toxic salts thereof, wherein
- (a) R is selected from the group consisting of alkoxy of one to six carbons, alkenyloxy of two to six carbons, alkyl of one to six carbons and benzyloxy;
- (b) $R_1$ and $R_2$ are each selected from the group consisting of hydrogen, alkoxy, alkenyloxy, benzyloxy and alkyl of one to six carbons;
- (c) $R_3$ and $R_4$ are each selected from the group consisting of hydrogen and alkyl of one to six carbon atoms;
- (d) $R_5$ is hydrogen or $R_5$ together with $R_3$ or $R_4$ represent methylene, and
- (e) n signifies the number 0 or 1, may be used most appropriately for the control or prevention of thrombus formation.

The compounds according to formula I herein referred to possess no noteworthy anti-inflammatory activity, which is in agreement with the conclusions of the article in 13, J. MED. CHEM. 211 (1970) where it is stated that for the possession of good anti-inflammatory activity it is essential that the carbohydroxamic acid function is only separated from the benzene ring by one carbon atom.

DESCRIPTION OF THE PREFERRED EMBODIMENTS

The hydroxamic acids according to the present invention are prepared in a way which is generally known for the preparation of hydroxamic acids.

The most usual method for the preparation of the hydroxamic acids concerned consists of the reaction of a carboxylic acid with the general formula:

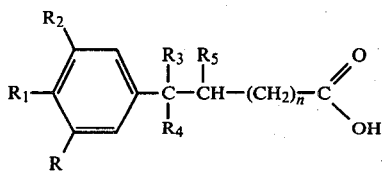
(II)

or an ester, acid halide or anhydride thereof, where R, R$_1$, R$_2$, R$_3$, R$_4$, R$_5$ and n have the meanings assigned above, with hydroxylamine. See Example I incorporated herein by reference.

The condensation of the free acid according to formula II with hydroxylamine is preferably performed in the presence of a dehydrating agent, for example a carbodi-imide such as dicyclohexylcarbodi-imide.

In the condensation of an ester according to formula II with hydroxylamine use is preferably made of a lower aliphatic ester of from one to six carbon atoms such as the methyl, ethyl, isopropyl, propyl, butyl, pentyl, or hexyl ester. (See Example I and II).

The starting compounds according to the general formula II and the esters, acid halides and anhydrides derived from these compounds are known. They may be prepared in obvious ways known to those skilled in the art.

For example, acids of formula II where n is 0, and R$_3$ and R$_4$ represent hydrogen may be prepared by catalytic reduction of the corresponding cinnamic acid derivative. Compounds according to formula II in which n is 0 or 1, and at least one of R$_3$ and R$_4$ represents hydrogen, may be prepared by a Wittig reaction (at from about −20° C. to about 80° C. and at a pressure of about 0.5 atm to about 1.5 atm) of the appropriate Wittig reagent with a benzaldehyde or phenylalkylketone (derived for example from acetophenone), substituted in the phenyl nucleus, followed by catalytic reduction of the unsaturated compound obtained at a temperature of from about −20° C. to about 120° C. and a pressure from about 1 atm to about 10 atm. Compounds according to formula II in which both R$_3$ and R$_4$ represent an alkyl group may for example be prepared by (a) halogenating a 1,1-dialkylbenzyl alcohol substituted in the phenyl nucleus (for example, a 2-phenylisopropyl alcohol substituted in the phenyl nucleus), (b) converting the halide thus obtained into the corresponding nitrile with the aid of potassium or sodium cyanide, (c) subsequently hydrolysing the nitrile to the corresponding carboxylic acid (after which the carboxylic acid is reduced to the corresponding alcohol with, for example, lithium aluminium hydride and the entire procedure is repeated again once or twice).

Compounds according to formula II, in which R$_3$ and R$_5$ together represent a methylene group, may for example be prepared by reacting a styrene derivative (substituted in the phenyl nucleus) with diazo-acetic ester or by reacting a cinnamic-ester derivative or a β,γ-unsaturated butyric acid ester derivative with diazo-methane.

By an alkyl group in the definition of R, R$_2$, R$_3$ and R$_4$ is meant a branched or straight-chain alkyl group with from one to six carbon atoms, such as methyl, ethyl, propyl, isopropyl, butyl, isobutyl, tert. butyl, amyl, iso-amyl, tert. amyl, hexyl and isohexyl.

The alkyl part of the alkoxy group as meant in the definition of R, R$_1$ and R$_2$ has the same significance.

By an alkenyloxy group in the definition of R, R$_1$ and R$_2$ is meant an unsaturated hydrocarbon residue with two to six carbon atoms, such as vinyl, allyl, β-allyl, iso-allyl, 1-butenyl, 2-butenyl, 3-butenyl, iso-butenyl, 2-methylallyl, 1-pentenyl and 3,3-dimethylallyl groups.

The compounds according to the invention may be administered by the oral, rectal or parenteral routes in pharmaceutically effective amounts, preferably in a daily dosage of from about 0.01 to about 100 mg per kg body weight.

When mixed with suitable excipients, the compounds according to the invention may be compressed to give solid formulations such as pills, dragees, tablets or suppositories. Examples of suitable excipients are lactose, starch, magnesium stearate, etc. Optionally mixed with the usual pharmaceutical excipients, they may also be processed to give capsules. With the aid of suitable liquids, the compounds may furthermore be used as injection preparations in the form of sterile solutions, emulsions or suspensions.

Compounds according to the invention which are preferably used are those compounds according to the general formula I, in which n signifies the number zero, and R represents an alkoxy, preferably a methoxy group.

From this group of preferred compounds those, in which (a) R$_3$, R$_4$ and R$_5$ are hydrogen, or (b) R$_3$ is methyl and R$_4$ and R$_5$ are hydrogen, or (c) R$_3$+R$_5$ is methylene and R$_4$ is hydrogen, are particularly valuable.

Among these preferred compounds, those compounds which contain one further substituent in the para-position, in particular an alkoxy, alkenyloxy or benzyloxy group, are particularly preferred. A particularly valuable compound is the compound 3-(3,4-dimethoxyphenyl)propionohydroxamic acid.

The compounds according to the general formula I may be converted into pharmaceutically acceptable non-toxic salts. These salts which are also numbered among the compounds of the invention are prepared by reacting the acid of formula I with a suitable alkaline substance, such as an alkalimetalhydroxide. The sodium salts of the acids of formula I are preferred.

EXAMPLE I

Preparation of 3-(3,4-dimethoxyphenyl)propionohydroxamic acid. A solution of 8.44 g powdered 88% KOH (132.6 mmol) by weight in 25 ml methanol is added to a solution previously obtained by dissolving 6.15 g hydroxylamine HCl (88.4 mmol) in 40 ml methanol at 50° C. After standing for 3 minutes in an ice-bath, the resultant KCl is filtered off and the filtrate is added to 10.0 g methyl 3-(3,4-dimethoxyphenyl) propionate. After stirring for 20 hours at room temperature, solvent is removed by evaporation without increasing the temperature and the residue is neutralized with 6 N HCl. Extraction with ethyl acetate, evaporation to dryness and crystallization of the residue from chloroform-hexane gives 7.70 g 3-(3,4-dimethoxyphenyl)propionohydroxamic acid. Repeated crystallization from chloroform-hexane gives a substance of analytical purity with a melting point of 105°–106° C.; Rf in toluene-ethanol (8:2)=0.45 (on SiO$_2$). Generally, this condensation reaction may take place at a temperature of from about −20° C. to about 100° C. and at a pressure of from about 0.5 atm to about 5 atm.

EXAMPLE II

Preparation of 3-(3-methoxy-4-allyloxyphenyl) propionohydroxamic acid (a) 13.1 g methyl 3-(3-methoxy-4-hydroxyphenyl) propionate (62.4 mmol) is dissolved in 150 ml dry N,N-dimethylformamide (DMF). After addition of 4.0 g 88% KOH (62.7 mmol) to this solution, the whole is stirred for 30 minutes, after which 7.55 g allyl bromide (62.4 mmol) in 120 ml dry DMF is added dropwise over a 30-minute period. After stirring for 1½ hours at room temperature, the reaction mixture is poured out into 1700 ml saturated NaCl solution. Extraction with ethyl acetate, evaporation to dryness and chromatography on 150 g silica gel with toluene-ethyl acetate (95:5) as eluent gives 12.4 g methyl 3-(3-methoxy-4-allyloxyphenyl)propionate as an oil. Rf in toluene:ethyl-acetate (85.15)=0.5 on $SiO_2$.

(b) 12.4 g methyl 3-(3-methoxy-4-allyloxyphenyl) propionate is treated with hydroxylamine at conditions corresponding to that described in Example I. The yield of 3-(3-methoxy-4-allyloxyphenyl) propionohydroxamic acid is 11.5 g. Crystallization from a methanol-toluene mixture gives an analytically pure sample of melting point 94°–95° C.

EXAMPLE III

The following compounds are prepared in a way corresponding to that described in Example I:

3-(3,5-dimethoxyphenyl)propionohydroxamic acid; melting-point 92°–94° C.;

3-(3-methoxyphenyl)propionohydroxamic acid; melting-point 76°–77° C.;

3-(3,4-dimethylphenyl)propionohydroxamic acid; melting-point 95°–98° C.;

3-(3,4,5-trimethoxyphenyl)propionohydroxamic acid; melting-point 122°–123° C.;

3-(3-methoxy-4-butoxyphenyl)propionohydroxamic acid; melting-point 82°–83° C.;

2,3-methylene-3-(3,4-dimethoxyphenyl)propionohydroxamic acid; melting point 138° C.;

3-(3-methoxy-4-benzyloxyphenyl)propionohydroxamic acid; melting point 123°–124° C.;

3-(3-benzyloxy-4-methoxyphenyl)propionohydroxamic acid; Rf in methylene chloride:methanol (85:15)=0.58 on $SiO_2$;

4-(3,4-dimethoxyphenyl)butyrohydroxamic acid; melting point 121°–123° C.;

3-(3,4-dimethoxyphenyl)-3-methyl-propionohydroxamic acid; melting point 125°–127° C.

EXAMPLE IV

In order to illustrate that the inhibition of platelet aggregation is coupled to the compounds of formula I, test results of a number of related hydroxamic acids in the so-called "in-vivo screen filtration" test are given in this Example. In this test the effects of the compounds to be tested on aggregation of platelets induced in-vivo by adenosine-5'-diphosphate (ADP) are determined. The circulation of blood through the aorta of normal rats, (which have already been treated for 5 days with the substance being tested (or placebo)), is diverted to the outside of the body through a plastic tube. The plastic tube is attached to a micro-filter system ($20\mu$) containing heparin. The blood pressure in front of and behind this filter can be recorded at any desired time. By injecting an ADP solution immediately before the filter, platelet aggregation is induced at that point. Aggregates of platelets then partially block the filter system, causing a change in pressure across the filter. Two variables are measured: (a) the change in pressure across the filter (hereinafter aggregation index) and (b) the time necessary for the original pressure gradient to be restored (hereinafter normalisation time).

The changes in aggregation index and normalization time are expressed as percentages of the values found for the rats treated with placebo. The compounds 1 to 7 inclusive are hydroxamic acids claimed and are according to the invention.

Hydroxamic acid derivative

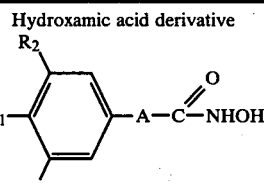

| No. | A | R | $R_1$ | $R_2$ | Dosage (oral) | Screen Filtration Test % change in Aggregation index | Normalisation time |
|---|---|---|---|---|---|---|---|
| 1. | —$CH_2$—$CH_2$— | $OCH_3$ | $OCH_3$ | H | 5 × 50 mg/kg | −23 | −24 |
| 2. | —$CH_2$—$CH_2$— | $OCH_3$ | H | $OCH_3$ | 5 × 50 mg/kg | −21 | −15 |
| 3. | —$CH_2$—$CH_2$— | $OCH_3$ | H | H | 5 × 50 mg/kg | −6 | −28 |
| 4. | $CH_3$<br>\|<br>—CH—$CH_2$— | $OCH_3$ | $OCH_3$ | H | 5 × 50 mg/kg | −10 | −42 |
| 5. | —$CH_2$—$CH_2$—$CH_2$— | $OCH_3$ | $OCH_3$ | H | 5 × 50 mg/kg | −8 | −19 |
| 6. | —CH——CH—<br>\\ /<br>$CH_2$ | $OCH_3$ | $OCH_3$ | H | 5 × 50 mg/kg | −22 | −37 |
| 7. | —$CH_2$—$CH_2$ | $OCH_3$ | $OCH_2C_6H_5$ | H | 5 × 50 mg/kg | −24 | −28 |
| 8. | —$CH_2$—$CH_2$— | H | $OCH_3$ | H | 5 × 50 mg/kg | −1 | +4 |
| 9. | —$CH_2$—$CH_2$ | $OCH_3$ | OH | H | 5 × 50 mg/kg | +10 | −3 |
| 10. | —CH=CH— | $OCH_3$ | $OCH_3$ | H | 5 × 100 mg/kg | −2 | 0 |
| 11. | —$CH_2$— | $OCH_3$ | $OCH_3$ | H | 5 × 50 mg/kg | +3 | −1 |

We claim:

1. A pharmaceutical composition having inhibitive and disaggregative properties towards blood platelet aggregation, comprising:

(A) a therapeutically effective amount to inhibit and disaggregate blood platelet aggregation of a compound of the formula:

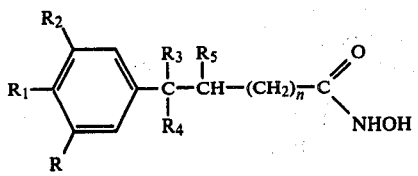

or a pharmaceutically acceptable non-toxic salt thereof, wherein:
(a) R is selected from the group consisting of alkoxy of one to six carbon atoms, alkenyloxy of two to six carbons and alkyl of one to six carbon atoms;
(b) $R_1$ and $R_2$ are each selected from the group consisting of hydrogen, alkoxy of one to six carbon atoms, alkenyloxy of two to six carbon atoms, alkyl from one to six carbon atoms, and benzyloxy;
(c) $R_3$ and $R_4$ are selected from the group consisting of hydrogen and alkyl of one to six carbon atoms;
(d) $R_5$ is hydrogen or together with $R_3$ and $R_4$ methylene, and
(e) n signifies the number 0 or 1; and
(B) a pharmaceutically acceptable carrier.

2. A method for inhibiting and disaggregating blood platelets in humans, which comprises administering to a human a pharmaceutical composition comprising:

(A) an amount effective to inhibit and disaggregate blood platelets in said human of a compound of the formula:

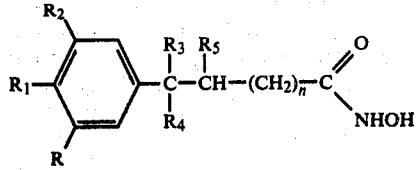

or a pharmaceutically acceptable non-toxic salt thereof, wherein:
(a) R is selected from the group consisting of alkoxy of one to six carbon atoms, alkenyloxy of two to six carbon atoms and alkyl of one to six carbon atoms;
(b) $R_1$ and $R_2$ are each selected from the group consisting of hydrogen, alkoxy of one to six carbon atoms, alkenyloxy of two to six carbon atoms, alkyl from one to six carbon atoms, and benzyloxy;
(c) $R_3$ and $R_4$ are selected from the group consisting of hydrogen and alkyl of one to six carbon atoms;
(d) $R_5$ is hydrogen or together with $R_3$ and $R_4$ methylene, and
(e) n signifies the number 0 or 1; and
(B) a pharmaceutically acceptable carrier.

3. The method of claim 2 wherein the compound is administered in a range effective amount is from about 0.01 to about 100 mg per kg body weight.

* * * * *